US00PP31305P2

(12) United States Plant Patent
Pineau

(10) Patent No.: US PP31,305 P2
(45) Date of Patent: Dec. 31, 2019

(54) ***HIBISCUS* PLANT NAMED 'MINSYRE10'**

(50) Latin Name: *Hibiscus syriacus*
Varietal Denomination: MINSYRE10

(71) Applicant: Patrick Pineau, Saint Mathurin sur Loire (FR)

(72) Inventor: Patrick Pineau, Saint Mathurin sur Loire (FR)

(73) Assignee: Hortival Diffusion SAS (FR)

( * ) Notice: Subject to any disclaimer, the term of this patent is extended or adjusted under 35 U.S.C. 154(b) by 0 days.

(21) Appl. No.: 16/350,722

(22) Filed: Dec. 20, 2018

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ..... A01H 5/02; A01H 6/60
See application file for complete search history.

*Primary Examiner* — Annette H Para
(74) *Attorney, Agent, or Firm* — Cassandra Bright

(57) ABSTRACT

A new and distinct *Hibiscus* cultivar named 'MINSYRE10' is disclosed, characterized by large, single, dark magenta flowers with a darker eye, up to 11 cm in diameter. Plants are well-branched, upright and vigorous and have been observed to have some resistance to Sclerotinia. The new variety is a *Hibiscus*, normally produced as an outdoor garden or container plant.

3 Drawing Sheets

Figure 1:
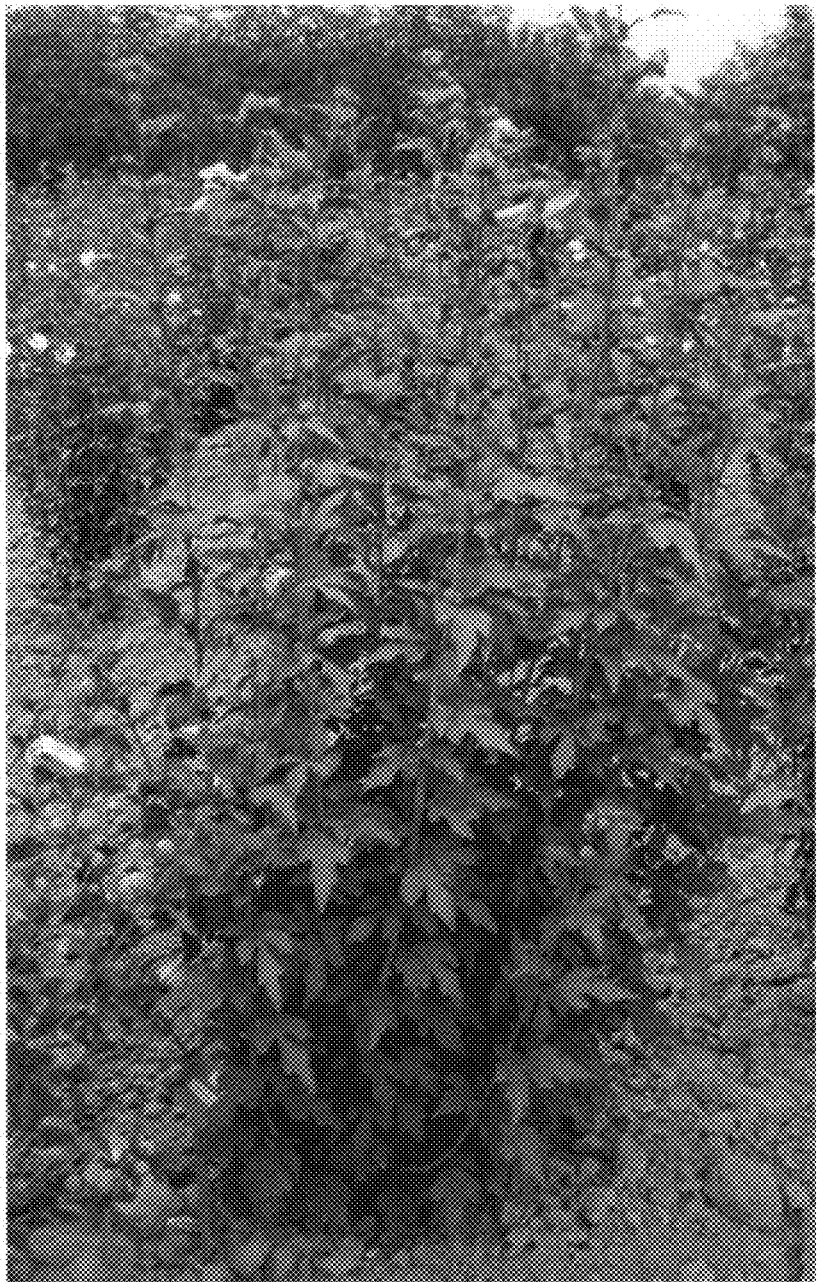

Latin name of the genus and species: *Hibiscus syriacus*.
Variety denomination: 'MINSYRE10'.

BACKGROUND OF THE INVENTION

The new *Hibiscus* cultivar is a product of a planned breeding program conducted by the inventor, Patrick Pineau. The objective of the breeding program was to vigorous *Hibiscus syriacus* cultivars with healthy foliage. The cross resulting in this new variety was made during 2008.

The seed parent is the unpatented *Hibiscus syriacus* 'Flogu'. The pollen parent is the unpatented variety *Hibiscus syriacus* 'Freedom'. The new variety was identified and selected as a potentially interesting selection in September 2012. Selection was made at a nursery in La Menitre, France.

Asexual reproduction of the new cultivar 'MINSYRE10' was first performed in January 2013 in La Menitre, Maine Et Loire, France, by grafting. Subsequent propagation has shown that the unique features of this cultivar are stable and reproduced true to type in 6 successive generations.

SUMMARY OF THE INVENTION

The cultivar 'MINSYRE10' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINSYRE10' These characteristics in combination distinguish 'MINSYRE10' as a new and distinct *Hibiscus* cultivar:

1. Dark magenta flower.
2. Large single flower.
3. Erect plant form.
4. Well branched.

5. Vigorous.
6. Some observed resistance to Sclerotinia.

PARENT COMPARISON

Plants of the new cultivar 'MINSYRE10' are similar to plants of the seed parent variety in most horticultural characteristics, however, plants of the new cultivar 'MINSYRE10' differ in the following;

1. Minsyre10 is more vigorous and has more branches than the seed parent.
2. Minsyre10 has longer and larger leaves than the seed parent.
3. Minsyre10 has less leaf blade lobing than the seed parent.
4. Minsyre10 has longer and larger petals than the seed parent.
5. Minsyre10 has a dark red purple petal color, the seed parent has a more purple petal color.
6. Minsyre10 has a darker red basal blotch than the seed parent.

Plants of the new cultivar 'MINSYRE10' are similar to plants of the pollen parent variety in most horticultural characteristics, however, plants of the new cultivar 'MINSYRE10' differ in the following;

1. Minsyre10 is more vigorous with more branches than pollen parent.
2. Minsyre10 has more lobing on the leaf blade than the pollen parent.
3. Minsyre10 is a single flower, the pollen parent has a double flower.
4. Minsyre10 has better pest resistance to Sclerotinia than the pollen parent.

COMMERCIAL COMPARISON

Plants of the new cultivar 'MINSYRE10' can be compared to the variety *Hibiscus* HAWAII 'Woodbridge', unpatented. These varieties are similar in most horticultural characteristics however, 'MINSYRE10' differs in the following:

1. Minsyre10 is more vigorous and with more branches than 'Woodbridge'.
2. Minsyre10 has darker red-purple petals than 'Woodbridge'.
3. Minsyre10 has more overlapping petals than 'Woodbridge'.
4. Minsyre10 has longer and larger petals than 'Woodbridge'.

BRIEF DESCRIPTION OF THE PHOTOGRAPHS

The accompanying photograph in FIG. 1 illustrates in full color a typical plant of 'MINSYRE10' grown in the ground at approximately 3 years old in La Minetre, France.

Figure 2:
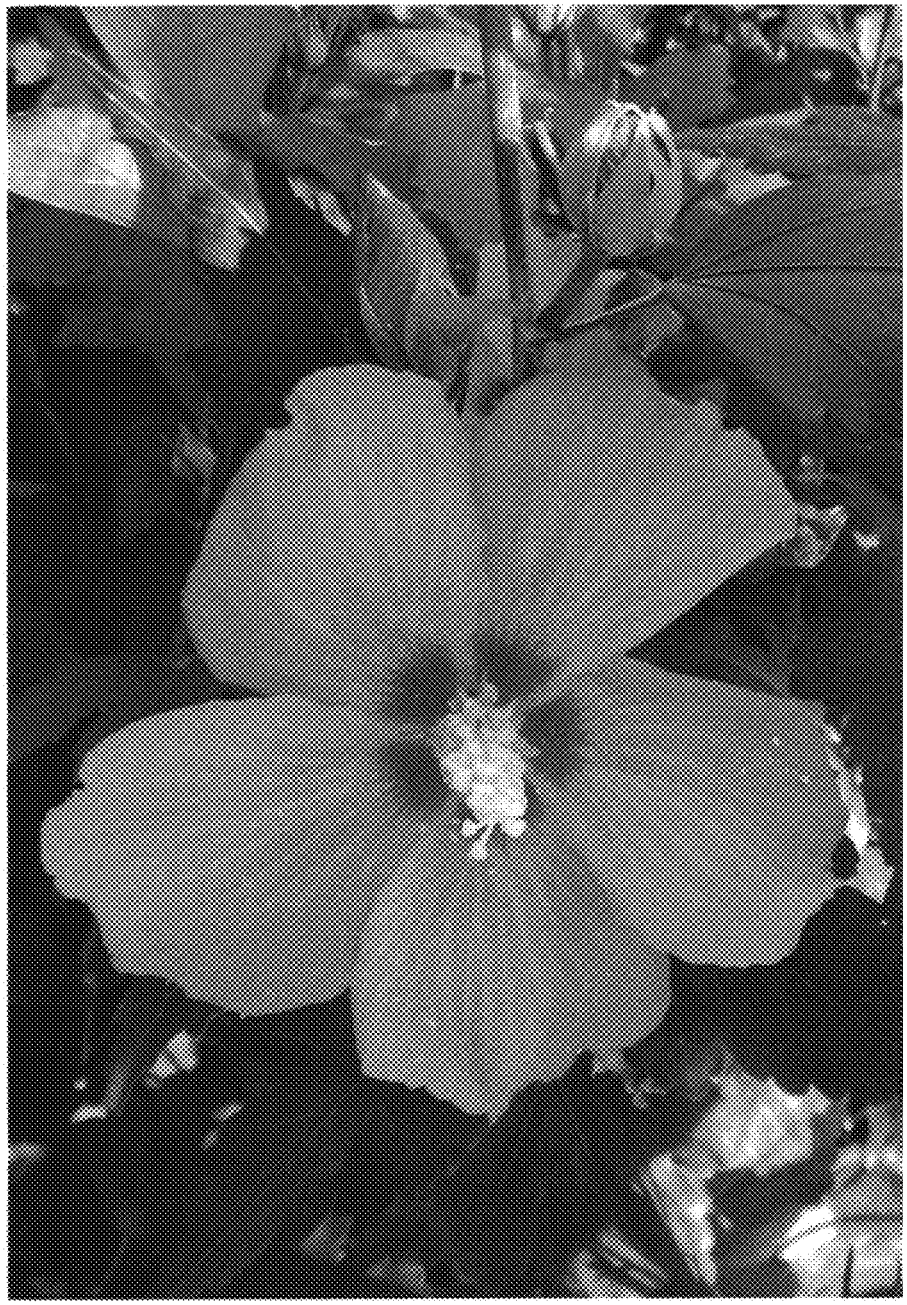

FIG. 2 illustrates in full color a typical flower of 'MINSYRE10'.

Figure 3:
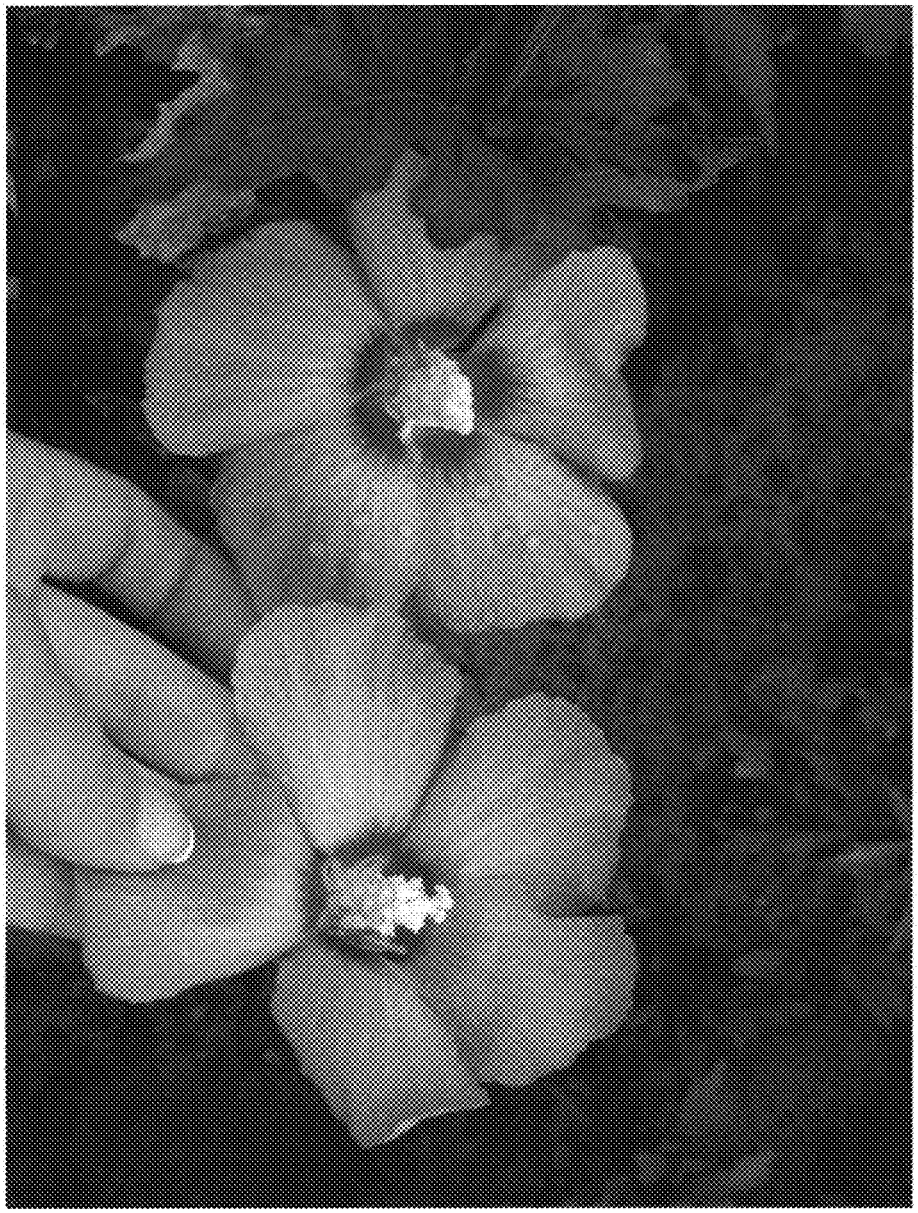

FIG. 3 compares a flower of 'MINSYRE10', on the top of the figure, to a flower of 'Woodridge', on the bottom of the photo. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'MINSYRE10' plants grown in an unheated polyhouse in Menitre, France under natural lighting. Measurements were taken during the August of 2018. The plants were about 3 years old in 4.5 liter containers. The growing temperature ranged from approximately −5° C. to 27° C. Measurements and numerical values represent averages of typical plant types.

Botanical Classification: *Hibiscus syriacus* 'MINSYRE10'.

PROPAGATION

Time to Initiate Roots: 20 days at approximately 25° C.

Root Description: Fibrous, medium root thickness. Tan/brown in color, not effectively measured with a color chart.

Time to Produce a Rooted Young Plant: About 90 days at 25° C.

PLANT

Plant Type: Perennial, hardy deciduous flowering shrub.

Age of Plant Described: Approximately 3 years old.

Growth Habit: Upright and vigorous.

Height: 100 cm.

Branching Characteristics: Well branched.

Length of Primary Lateral Branches: 90 cm.

Quantity of Lateral Branches: 8.

Characteristics of Primary Lateral Branches:

*Diameter.*—0.4 cm.

*Color.*—RHS Yellow-Green 147C.

Internode Length: 5 cm.

FOLIAGE

Leaf:

*Arrangement.*—Alternate.

*Quantity.*—Approximately 25 per branch.

*Average Length.*—11 cm.

*Average Width.*—6 cm.

*Shape of blade.*—Ovate, 3-lobed.

*Apex.*—Acute.

*Base.*—Obtuse.

*Margin.*—Lobed, crenate.

*Texture of top surface.*—Glabrous.

*Texture of bottom surface.*—Rough, with sparse adpressed hairs along veins.

*Color.*—Young foliage upper side: RHS Green 137R. Young foliage under side: RHS Yellow-Green 144C. Mature foliage upper side: RHS Green 137A. Mature foliage under side: RHS Yellow-Green 144C.

*Fall or Winter coloration variance.*—Mature foliage upper side: None. Mature foliage under side: None.

*Venation.*—Type: Pinnate. Venation color upper side: RHS Yellow-Green 145A. Venation color under side: RHS Green 137B.

*Petiole.*—Length: 1.8 cm. Diameter: 0.2 cm. Color: RHS Yellow-Green 138A.

FLOWER

Natural Flowering Season: July to September.

Flower Type and Habit: Solitary, rotate.

*Single, double, multiplex.*—Single.

*Petals overlapping.*—Overlapping.

Rate of Flower Opening: 1 to 2 days from bud to fully opened flower.

Flower Longevity on Plant: 1 to 2 days.

Persistent or Self-Cleaning: Self-cleaning.

Bud:

*Shape.*—Ovate.

*Length.*—2 cm.

*Diameter.*—1.1 cm.

*Color.*—RHS Red-Purple 59A.

Flower Size:

*Diameter.*—11 cm.

*Depth.*—3 cm.

Petals:

*Quantity.*—5.

*Arrangement.*—Rotate.

*Length.*—6 cm.

*Width.*—5.5 cm.

*Shape.*—Rounded deltoid.

*Apex.*—Rounded, irregular shallow indentations.

*Base.*—Obovate.

*Margin.*—Entire.

*Texture, upper and lower surfaces.*—Color: When opening, upper surface: RHS Red-Purple 63A with darker edge blush near 64A. When opening, lower surface: RHS Red-Purple 63A with darker edge blush near 64A. Veins near 63D. Fully opened, upper surface: RHS Red-Purple 63B with darker edge blush near 64A. Fully opened, lower surface: RHS Red-Purple 63A with darker edge blush near 64A. Streaked near 63D. Color basal blotch: RHS Red-Purple 59A. Ratio of basal blotch/petal size: About 25% of petal blade blotched. Feathering color: RHS Red-Purple 59A. Feathering size: 0.4 to 1 cm.

Sepals:
*Quantity.*—5 to 6.
*Length.*—2 cm.
*Width.*—0.8 cm.
*Shape.*—Ovate.
*Margin.*—Entire.
*Color.*—RHS Green 143C.
Peduncles:
*Length.*—1 cm.
*Diameter.*—0.3 cm.
*Angle.*—About 45° to the lateral branch.
*Strength.*—Strong.
*Texture.*—Glabrous.
*Color.*—RHS Green 143C.
Fragrance: None.

REPRODUCTIVE ORGANS

Stamens:
*Number.*—50.
Anthers:
*Shape.*—Irregular sphere.
*Length.*—0.3 cm.
*Color.*—Near RHS White 155D.
*Pollen color.*—RHS Yellow 4D.
*Pollen amount.*—Abundant.

Pistil:
*Number.*—1.
*Length.*—3.5 cm.
*Style.*—Length: 3 cm. Color: Near RHS White 155C.
*Stigma.*—Shape: Rounded disc. Color: Near RHS White 155C.
*Ovary color.*—Near RHS Yellow-Green 145C.

OTHER CHARACTERISTICS

Seeds: Capsule, typically about 1 cm in diameter and length. Pubescent, colored near Grey-Brown 199B. Moderately abundant lightly pubescent seed.
Disease/Pest Resistance: Improved resistance to Sclerotinia. No other resistance nor susceptibility to normal diseases and pests of *Hibiscus syriacus* have been observed.
Temperature Tolerance: Low temperature tolerance to at least USDA zone 4, high temperature tolerance to at least 40° C.

What is claimed is:

1. A new and distinct cultivar of *Hibiscus* plant named 'MINSYRE10' as herein illustrated and described.

* * * * *